(12) United States Patent  
Panken et al.

(10) Patent No.: US 11,135,429 B2
(45) Date of Patent: Oct. 5, 2021

(54) NEURAL OSCILLATORY SIGNAL SOURCE LOCATION DETECTION

(71) Applicant: Medtronic, Inc., Minneapolis, MN (US)

(72) Inventors: Eric J. Panken, Edina, MN (US); Christopher L. Pulliam, Plymouth, MN (US); Jadin C. Jackson, Roseville, MN (US); Yizi Xiao, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 75 days.

(21) Appl. No.: 16/395,308

(22) Filed: Apr. 26, 2019

(65) Prior Publication Data
US 2020/0338351 A1 Oct. 29, 2020

(51) Int. Cl.
*A61B 5/00* (2006.01)
*A61B 5/24* (2021.01)
(Continued)

(52) U.S. Cl.
CPC ........ *A61N 1/36139* (2013.01); *A61B 5/7221* (2013.01); *A61N 1/0534* (2013.01);
(Continued)

(58) Field of Classification Search
CPC ............ A61N 1/36139; A61N 1/36153; A61N 1/0534; A61N 1/37235; A61N 1/0529; A61N 1/0531; A61N 1/36025; A61N 1/36062; A61N 1/36067; A61N 1/36071; A61N 1/36075; A61N 1/36082; A61N 1/36085; A61N 1/36092; A61N 1/36096;
(Continued)

(56) References Cited

U.S. PATENT DOCUMENTS

2007/0179558 A1 * 8/2007 Gliner ................ A61N 1/36082
607/45
2011/0040547 A1 2/2011 Gerber et al.
(Continued)

FOREIGN PATENT DOCUMENTS

WO WO-2016196790 A1 * 12/2016 ........... A61B 5/4836

OTHER PUBLICATIONS

Lempka et al., "Theoretical Analysis of the Local Field Potential in Deep Brain Stimulation Applications," PLOS One Journal, Mar. 28, 2013, 14 pp.
(Continued)

*Primary Examiner* — Carl H Layno
*Assistant Examiner* — Anh-Khoa N Dinh
(74) *Attorney, Agent, or Firm* — Shumaker & Sieffert, P.A.

(57) ABSTRACT

Techniques are described to determine a location of at least one oscillatory signal source in a patient. Processing circuitry may determine expected electrical signal levels based on a hypothetical location of the at least one oscillatory signal source. Processing circuitry may determine the electrical signal levels and determine an error value based on the expected electrical signal levels and the determined electrical signal levels. Processing circuitry may adjust the hypothetical location of the at least one oscillatory signal source until the error value is less than or equal to a threshold value, including the example where the error value is minimized.

25 Claims, 5 Drawing Sheets

(51) Int. Cl.
    *A61B 5/369*     (2021.01)
    *A61N 1/05*     (2006.01)
    *A61N 1/36*     (2006.01)
    *A61N 1/372*     (2006.01)
    *G01B 7/00*     (2006.01)
    *G16H 20/30*     (2018.01)
    *G16H 50/20*     (2018.01)
    *G16H 50/50*     (2018.01)

(52) U.S. Cl.
    CPC ..... *A61N 1/36153* (2013.01); *A61N 1/37235* (2013.01); *G01B 7/003* (2013.01)

(58) Field of Classification Search
    CPC ............ A61N 1/36103; A61N 1/36185; A61B 5/7221; A61B 5/24; A61B 5/369; A61B 5/40; A61B 5/4836; A61B 5/4094; G01B 7/003; G01H 20/30; G01H 50/20; G01H 50/50
    See application file for complete search history.

(56) References Cited

U.S. PATENT DOCUMENTS

| | | |
|---|---|---|
| 2011/0144521 A1 | 6/2011 | Molnar et al. |
| 2011/0264165 A1* | 10/2011 | Molnar .............. A61N 1/36185 607/45 |
| 2011/0264171 A1* | 10/2011 | Torgerson .......... A61N 1/36146 607/59 |
| 2014/0005518 A1 | 1/2014 | Ko et al. |
| 2016/0051812 A1 | 2/2016 | Montgomery, Jr. et al. |
| 2016/0081577 A1* | 3/2016 | Sridhar .................. A61B 5/742 600/383 |
| 2016/0144186 A1* | 5/2016 | Kaemmerer ....... A61N 1/36096 607/45 |
| 2017/0259064 A1* | 9/2017 | Wu ...................... A61B 5/4076 |

OTHER PUBLICATIONS

International Search Report and Written Opinion from International Application No. PCT/US2020/025995, dated Jul. 10, 2020, 10 pp.

* cited by examiner

NEURAL OSCILLATORY SIGNAL SOURCE LOCATION DETECTION

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device delivers electrical stimulation therapy via one or more leads that include electrodes located proximate to target locations associated with the brain, the spinal cord, pelvic nerves, peripheral nerves, or the gastrointestinal tract of a patent. For bipolar stimulation, the electrodes used for stimulation may be on one or more leads. For unipolar stimulation, the electrodes may be on one or more leads, and an electrode on a stimulator housing located remotely from the target site (e.g., near clavicle). It may be possible to use leadless stimulation using electrodes mounted on the stimulation housing. Hence, electrical stimulation is used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current pulse amplitude, a pulse width, and a pulse frequency as stimulation parameters. A set of parameters, such as a set including electrode combination, electrode polarity, amplitude, pulse width, and pulse rate, may be referred to as a program in the sense that they define the electrical stimulation therapy to be delivered to the patient.

SUMMARY

This disclosure describes example techniques to determine a location of an oscillatory signal source within a brain of a patient. In the example techniques, a medical device (e.g., implantable medical device (IMD) or programmer) may be configured to compare actual measurements of electrical signals formed on electrodes due to the signal generated by the oscillatory signal source with expected (e.g., theoretical or modeled) measurements of the electrical signals. The expected measurements may be based on a hypothetical location of the oscillatory signal source. The medical device may keep adjusting the hypothetical location of the oscillatory signal source to such that the difference between the actual measurements and the expected measurements are iteratively reduced below a threshold (e.g., minimized). The medical device may determine that the hypothetical location of the oscillatory signal source where the difference between the expected measurements and the actual measurements is below a threshold (e.g., minimized) is the location of the oscillatory signal. Based on the determined location of the oscillatory signals source, the medical device may determine which electrodes to use for therapy delivery (e.g., electrodes most proximate to the oscillatory signal source).

In one example, this disclosure describes a method comprising determining electrical signal levels at or across a plurality of electrodes implanted in tissue of a patient, wherein the electrical signal levels are generated by at least one oscillatory signal source in the tissue of the patient, determining, based on a hypothetical location of the at least one oscillatory signal source, expected electrical signal levels at the plurality of electrodes, determining an error value based on the determined electrical signal levels and the expected electrical signal levels, repeatedly adjusting the hypothetical location, and repeatedly determining the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value, and generating information indicative of the location of the at least one oscillatory signal source.

In one example, this disclosure describes a medical device comprising a memory configured to store information indicative of electrical signal levels at or across a plurality of electrodes implanted in tissue of a patient and processing circuitry. The processing circuitry is configured to determine the electrical signal levels based on the stored information, determine, based on a hypothetical location of the at least one oscillatory signal source, expected electrical signal levels at the plurality of electrodes, determine an error value based on the determined electrical signal levels and the expected electrical signal levels, repeatedly adjust the hypothetical location, and repeatedly determine the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value, and generate information indicative of the location of the at least one oscillatory signal source.

In one example, the disclosure describes a system comprising one or more leads comprising electrodes implanted in tissue of a patient, a sensing circuitry configured to sense electrical signal levels at or across a plurality of the electrodes, and processing circuitry. The processing circuitry is configured to determine the electrical signal levels based on information indicative of the sensed electrical signals from the sensing circuitry, determine, based on a hypothetical location of at least one oscillatory signal source, expected electrical signal levels at the plurality of electrodes, determine an error value based on the determined electrical signal levels and the expected electrical signal levels, repeatedly adjust the hypothetical location, and repeatedly determine the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value, and generate information indicative of the location of the at least one oscillatory signal source.

In one example, this disclosure describes a computer-readable storage medium comprising instructions stored thereon that when executed one or more processors of a medical device to determine electrical signal levels at or across a plurality of electrodes implanted in tissue of a patient, wherein the electrical signal levels are generated by at least one oscillatory signal source in the tissue of the patient, determine, based on a hypothetical location of the at least one oscillatory signal source, expected electrical signal levels at the plurality of electrodes, determine an error value based on the determined electrical signal levels and the expected electrical signal levels, repeatedly adjust the hypothetical location, and repeatedly determine the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value, and generate information indicative of the location of the at least one oscillatory signal source.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
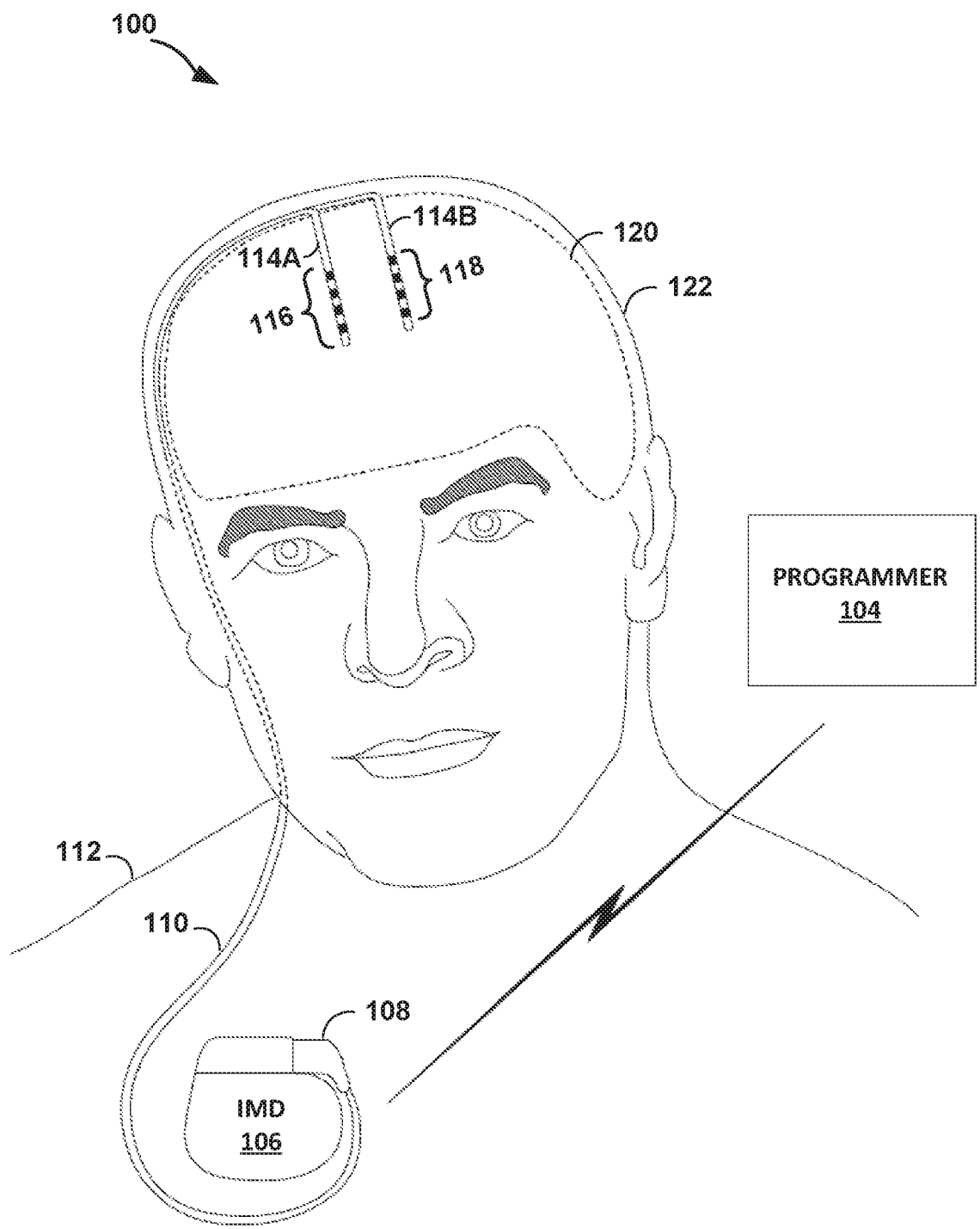
FIG. 1 is a conceptual diagram illustrating an example system that includes an implantable medical device (IMD) configured to deliver adaptive DBS to a patient according to an example of the techniques of the disclosure.

This disclosure describes example techniques to define a location of an oscillatory signal source based on comparison of actual measurements of an electrical signal and expected (e.g., theoretical or modeled) measurements of the electrical signal. The example techniques utilize regression formulas (e.g., least squares formulation) to determine coordinates for the oscillatory signal source that iteratively reduce error between actual measurements and expected measurements to a threshold error level. In some examples, the example techniques may determine coordinates for the oscillatory signal source that minimize the error between actual measurements and expected measurements. For example, a medical device may measure voltages across electrodes, where the voltages are generated by the oscillatory signal source outputting a current. The medical device may also determine what the voltage across the electrodes should be (e.g., expected voltage) given a hypothetical (e.g., assumed) location of the oscillatory signal source. An error value may be the difference between the measured voltage and the expected voltage, and the medical device may update coordinates of the oscillatory signal source to reduce the error value, e.g., by iterative updates to reduce the error value. In some examples, the medical device may update the coordinates to minimize or approximately minimize the error.

One example way to determine what the voltage across the electrodes should be (e.g., expected voltage) given a hypothetical location of the oscillatory signal is based on lead-field model values that define what the voltage should be based on coordinates of the oscillatory signal source. The lead-field model values multiplied by the charge value of the oscillatory signal source should be equal to the measured voltage.

The charge value of the signal source may be unknown. However, an expected charge value of the signal source can be calculated based on the measured voltages and the lead-field model values. The expected voltage may be the expected charge value multiplied by the lead-field model values.

As one example, assume that there are N electrodes located at R1 to RN, respectively. The measured voltages at each of these electrodes is V(R1) to V(RN), respectively. Also, assume there is a single oscillatory signal source. The lead-field values for the N electrodes is equal to G(R1, r) to G(RN, r), where r is the hypothetical location of the oscillatory signal source. In this example, V(R1) to V(RN) can be assumed as a 1×N sized matrix, and G(R1, r) to G(RN, r) can be assumed to be a 1×N sized matrix.

The expected charge value (referred to as Q') of the signal source can be represented as: $Q'=(G^TG)^{-1}G^TV$, where G and V represent the respective 1×N matrices. The expected voltage for the hypothetical location of r for the oscillatory signal source is $G*Q'$. The error value may be represented as $norm(V-G*Q')$. The medical device may update the coordinates for r until the error value is minimized.

In the above example, only one oscillatory signal source was assumed. However, the techniques are extendable to examples where multiple oscillatory signal sources are present. Also, the above example assumed the oscillatory signal source to be a point charge. However, the techniques are extendable to examples including dipole oscillatory signal sources.

Moreover, in the above examples, the voltage at an electrode was utilized for the calculations. However, in some cases, the voltage measurements may represent the voltage across electrodes (e.g., bipolar measurement) and not the voltage at an electrode relative to ground (e.g., unipolar measurement). In some examples, to determine the voltages, the medical device may short segmented electrodes at the same axial location, i.e., z-distance, on a lead to allow bipolar measurements to be taken across the shorted segmented electrodes and ring electrodes. The medical device may determine bipolar measurements across segmented electrodes that are not shorted. In this example, the medical device may not determine bipolar measurements across a segmented electrode and a ring electrode.

Also, although the above example is described with respect to a single source, the example techniques may be extended to where there are multiple sources. For instance, the algorithm described in this disclosure may be run multiple times across multiple frequency sub-bands to detect locations of multiple sources that might appear as one big source.

Based on the above techniques, the medical device may determine a relative location of the one or more oscillatory sources. Based on the determined location of the one or more oscillatory sources, the medical device may select which electrodes to use for therapy delivery. For example, the electrodes that are proximate (e.g., most proximate among the electrodes) may be a better suited to deliver therapy as compared to other electrodes. Also, the medical device may be configured to determine (e.g., estimate or recommend) therapy parameters based on the relative location of the one or more oscillatory sources.

FIG. 1 is a conceptual diagram illustrating an example system 100 that includes an implantable medical device (IMD) 106 configured to deliver adaptive deep brain stimulation (DBS) to a patient 112. DBS may be adaptive in the sense that IMD 106 may adjust, increase, or decrease the magnitude of one or more parameters of the DBS in response to changes in patient activity or movement, a severity of one or more symptoms of a disease of the patient, a presence of one or more side effects due to the DBS, or one or more sensed signals of the patient.

For instance, one example of system 100 is a bi-directional DBS system with capabilities to both deliver stimulation and sense intrinsic neuronal signals. System 100 provides for "closed-loop" therapy where IMD 106 may continuously monitor the state of certain biomarker signals and deliver stimulation according to pre-programmed routines based on the biomarker signals.

System 100 may be configured to treat a patient condition, such as a movement disorder, neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120. In some examples, unipolar stimulation may be possible where one electrode is on the housing of IMD 106.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, the neurological signals sensed within brain 120 may reflect changes in electrical current produced by the sum of electrical potential differences across brain tissue. Examples of neurological brain signals include, but are not limited to, bioelectric signals generated from local field potentials (LFP) sensed within one or more regions of brain 120. Electroencephalogram (EEG) signal or an electrocorticogram (ECoG) signal are also examples of bioelectric signals. For example, neurons generate the bioelectric signals, and if measured at depth, it is LFP, if measured on the coretex, it is ECoG, and if on scalp, it is EEG. In this disclosure, the term "oscillatory signal source" is used to describe a signal source that generates bioelectric signals.

One example of the feature of interest (e.g., biomarker) within the LFPs is synchronized beta frequency band (13-33 Hz) LFP activity recorded within the sensorimotor region of the subthalamic nucleus (STN) in Parkinson's disease patients. The source of the LFP activity can be considered as an oscillatory signal source, within the brain of the patient, that outputs an oscillatory electrical voltage signal that is sensed by one or more of electrodes 116 and/or 118. The suppression of pathological beta activity (e.g., suppression or squelching of the signal component of the bioelectric signals generated from the oscillatory LFP signal source that is within the beta frequency band) by both medication and DBS may correlate with improvements in the motor symptoms of patients who have Parkinson's disease.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, both stimulation electrode combinations and sense electrode combinations may be selected from the same set of electrodes 116, 118. In other examples, the electrodes used for delivering electrical stimulation may be different than the electrodes used for sensing neurological brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a selected therapy program. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes.

In some examples, electrodes 116, 118 may be radially-segmented DBS arrays (rDBSA) of electrodes. Radially-segmented DBS arrays refer to electrodes that are segmented radially along the lead. As one example, leads 114A and 114B may include a first set of electrodes arranged circumferentially around leads 114A and 114B that are all at the same height level on leads 114A and 114B. Each of the electrodes in the first set of electrodes is a separate segmented electrode and form a level of radially-segmented array of electrodes. Leads 114A and 114B may include a second set of electrodes arranged circumferentially around leads 114A and 114B that are all at the same height level on leads 114A and 114B. Each of the electrodes in the first set of electrodes is a separate segmented electrode and form a level of radially-segmented array of electrodes. The rDBSA electrodes may be beneficial for directional stimulation and sensing.

The signal component in the beta frequency band is described as one example, and the techniques are applicable to other types of LFP activity. Furthermore, the example techniques are not limited to examples where electrodes 116, 118 are an rDBSA of electrodes. The example of using rDBSA of electrodes is described as a way of directional stimulation and sensing. However, the example techniques are also useable in examples where directional stimulation and sensing are not available or are not used. Moreover, there may be other ways of performing directional stimulation and sensing that do not require the use of an rDBSA of electrodes.

To suppress the signal component having the beta frequency band from the oscillatory signal source, IMD 106 may output an electrical stimulation signal that alters the way in which neurons of the oscillatory signal source produce signals. For example, the electrical stimulation either directly inhibits a certain neuronal population that includes the oscillatory signal source or excites one group of neurons which in turn suppresses another group of neurons (e.g., network effect). The stimulation may act on the neurons directly, and not necessarily on the signals the neurons (e.g., oscillatory signal source) produces.

As described in more detail, algorithms may be used to determine the most proximal electrodes of electrodes 116 and 118 to the oscillatory signal source. In general, the electrodes of electrodes 116 and 118 that are most proximal to the oscillatory source tend to be the electrodes with which electrical stimulation should be delivered. This disclosure describes example techniques to determine a location of the oscillatory signal source and based on the location of the oscillatory signal source, IMD 106 or programmer 104 may determine which electrodes 116 and 118 are most proximate to the oscillatory signal source.

To determine the location of the oscillatory signal source, IMD 106 may determine the electrical signal levels (e.g., voltage levels) at electrodes 116, 118. In some examples, the voltage levels may be based on bipolar measurements (e.g., across neighboring electrodes of electrodes 116 and/or 118). IMD 106 may also determine expected electrical signal levels based on a hypothetical location of the oscillatory signal source. For example, lead-field equations (also called electrical field equations) define a mathematical relationship between voltage and location of an oscillatory signal source. As one example, the voltage (V) at an electrode is equal to a distance scalar value multiplied by the charge (Q) of the oscillatory signal source, where the distance scalar value is based on a distance between the electrode and the location of the oscillatory signal source.

In one or more examples, IMD 106 may assign coordinate values to the oscillatory signal source as a way to determine a hypothetical location of the oscillatory signal source. Based on the coordinate values, IMD 106 may determine a matrix of distance scalar values based on a distance between one or more of electrodes 116, 118 and the hypothetical location of the oscillatory signal source. The matrix of distance scalar values is referred to as G, where G includes a first distance scalar value based on a distance between a first electrode of electrodes 116, 118 and the hypothetical location of the oscillatory signal source, a second distance scalar value based on a distance between a second electrode of electrodes 116, 118 and the hypothetical location of the oscillatory signal source, and so forth. One example of the distance scalar value is the inverse of the square of the distance between one or more of electrodes 116, 118 and the hypothetical location of the oscillatory signal source.

Based on the matrix of scalar values, it may be possible to determine the voltages at electrodes 116, 118 that are caused by the oscillatory signal source. For instance, the voltages at each respective one of electrodes 116, 118 is equal to its respective distance scalar value multiplied by Q (e.g., charge of the oscillatory signal source). In other words, voltage at first one of electrodes 116, 118 equals a first distance scalar value multiplied by Q, where the first distance scalar value is based on a distance between the first one of electrodes 116, 118 and the hypothetical location of the oscillatory signal source. Voltage at a second one of electrodes 116, 118 equals a second distance scalar value multiplied by Q, where the second distance scalar value is based on a distance between the second one of electrodes 116, 118 and the hypothetical location of the oscillatory signal source, and so forth.

However, the value of Q (e.g., charge of the oscillatory signal source) is unknown. Therefore, determining what the voltages at electrodes 116, 118 would be for a hypothetical location of the oscillatory signal source may be difficult. In accordance with one or more examples described in this disclosure, the value of Q (e.g., charge of the oscillatory signal source) may be estimated based on the matrix of distance scalar values (e.g., G) and the actual measured voltages. For instance, assume that the actual measured voltages at each one of one or more of electrodes 116, 118 is represented by a matrix V (e.g., a first value of matrix V is the actual measured voltage of a first one of electrodes 116, 118, a second value of matrix V is the actual measured voltage of a second one of electrodes 116, 118, and so forth). In this example, the expected value of Q (referred to as Q') is equal to $(G^T G)^{-1} G^T V$.

As described above, an electrical signal level (e.g., voltage level) at one or more electrodes 116, 118 caused by an oscillatory signal source is equal to the distance scalar values (e.g., G) multiplied by the charge of the oscillatory signal source (e.g., Q). In other words, voltage is equal to G*Q. Therefore, an expected electrical signal level (e.g., expected voltage level) at one or more electrodes 116, 118 is equal to G*Q'. The expected voltage level is referred to as V'.

For example, IMD 106 may determine a hypothetical location of the oscillatory signal source. The actual location of the oscillatory signal source is unknown, and so IMD 106 starts with a guess of the location of oscillatory signal source. This guess of the location of the oscillatory signal source is referred to as the hypothetical location of the oscillatory signal source. Based on the hypothetical location of the oscillatory signal source, IMD 106 may determine the matrix of distance scalar values (e.g., G) for one or more of electrodes 116, 118. Also, based on the actual measured voltages at one or more electrodes 116, 118 (e.g., matrix V), IMD 106 may determine an expected charge value (Q') of the oscillatory signal source (e.g. $Q'=(G^T G)^{-1} G^T V$). Based on the estimate of the charge value, IMD 106 may determine an expected voltage (V') for each of the one or more electrodes 116, 118 to form a matrix V'.

In this way, IMD 106 may determine an expected voltage level (V') at electrodes 116, 118 if the oscillatory signal source were at the hypothetical location. IMD 106 may determine an error value between the actual measured voltage levels (V) and the expected voltage levels (e.g., V−V').

In one or more examples, IMD 106 may adjust the hypothetical location and repeatedly determine the error value for each of the adjusted hypothetical locations of the oscillatory signal source until the determined error value is reduced to be less than or equal to a threshold value (which includes the example where the error value is minimized). As an example, assume that matrix $V'_1$ the expected electrical signal level for one or more electrodes 116, 118 when the oscillatory signal source is assumed to be at a first hypothetical location. In this example, a first error value is equal to $(V-V'_1)$. IMD 106 may update the hypothetical location of the oscillatory signal source from the first hypothetical location to a second hypothetical location (e.g., determine a new coordinate value for the oscillatory signal source). Assume that matrix $V'_2$ is the expected electrical signal level for one or more electrodes 116, 118 when the oscillatory signal source is assumed to be at the second hypothetical location. In this example, a second error value is equal to $(V-V'_2)$. IMD 106 may repeatedly determine error values until the error value is less than or equal to a threshold value, including examples where the error value is minimized.

The location of the oscillatory signal source is based on a hypothetical location for the oscillatory signal source for which the determined error value is less than or equal to the threshold value. For example, assume that the value of $(V-V'_2)$ is the minimal error value among all the error values calculated for different hypothetical locations of the oscillatory signal source. In this example, the actual location of the oscillatory signal source may be based on the second hypothetical location because the $V'_2$ is based on an assumption that the oscillatory signal source is located at the second hypothetical location. As one example, IMD 106 may determine that the actual location of the oscillatory signal source is equal to the second hypothetical location.

In this manner, IMD 106 may determine the location of the oscillatory signal source. Based on the location of the oscillatory signal source, IMD 106 may determine which ones of electrodes 116, 118 are most proximate to the oscillatory signal source. The determined electrodes of electrodes 116, 118 may be well suited for delivery of electrical stimulation.

In the above example, the error value is described as being the difference between V and V'. In some examples, V is a matrix of values and V' is a matrix of values. In such examples, the error value may be based on a comparison of each value in the V and V' matrix. For instance, IMD 106 may determine the norm(V−V'), where the "norm" function is indicative of a distance between values in the V and V' matrix. For example, norm(V−V') equals square root of ((first value of V−first value of V')$^2$+(second value of V−second value of V')$^2$+ . . . ).

One way for IMD 106 to adjust hypothetical locations is using a least mean square regression technique, although other techniques are possible. In the least mean regression technique, another way to represent minimizing the error value is to maximize the fit, where the fit is equal to −log 10(error value).

In the above example, it was assumed that there was one oscillatory signal source. However, the techniques are not so limited. In some examples, there may be a plurality of oscillatory signal sources. In such examples, IMD 106 may determine a two-dimensional matrix of G values (one value for each electrode for each oscillatory signal source) and determine a Q' value for each oscillatory signal source. The other operations may be the same.

Moreover, there may be different example types of oscillatory signal sources, such as point charge signal sources and dipole charge signal sources. The example techniques are applicable to both point and dipole charge signal sources. Examples for distance scalar values (e.g. G values) for point and dipole charge signal sources are described in more detail below.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres (or in just one hemisphere in some examples), respectively, of patient 112 in order to deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. For example, the target tissue site may be the location of the oscillatory signal source that generates the bioelectric signal having a signal component in the beta frequency band. The stimulation electrodes used to deliver stimulation to the target tissue site may be those that are most proximal to the oscillatory signal source, e.g., using the example techniques described in this disclosure. Other lead 114 and IMD 106 implant sites are contemplated. For example, IMD 106 may be implanted on or within cranium 122, in some examples. Leads 114A and 114B may be implanted within the same hemisphere or IMD 106 may be coupled to a single lead implanted in a single hemisphere, in some examples.

Existing lead sets include axial leads carrying ring electrodes disposed at different axial positions and so-called "paddle" leads carrying planar arrays of electrodes. Selection of electrode combinations within an axial lead, a paddle lead, or among two or more different leads presents a challenge to the clinician. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because ring electrodes are relatively simple to program and are capable of delivering an electrical field to any tissue adjacent to electrodes 116, 118. In other examples, electrodes 116, 118 may have different configurations. For example, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue.

In some examples, a housing of IMD 106 may include one or more stimulation and/or sensing electrodes. In some examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the parameters of the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combinations with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

However, in some examples, IMD 106 or programmer 104 (e.g., a medical device), alone or in combination, may automatically determine electrode configuration and therapy parameters. For example, the medical device may determine which electrodes to use for stimulation based on which electrodes are most proximal to the oscillatory signal source. In some examples, programmer 104 may output information indicating the selected electrode configuration for stimulation and the determined stimulation amplitude or other therapy parameter for the clinician or physician to review and confirm before IMD 106 delivers therapy via the selected electrode configuration with the determined stimulation amplitude.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112. Further, an IMD may provide other electrical stimulation such as spinal cord stimulation to treat a movement disorder.

According to the techniques of the disclosure, a medical device (e.g., IMD 106 or programmer 104 either alone or in combination) of system 100 may be configured to determine electrical signal levels (e.g., voltage levels) at or across a plurality of electrodes 116, 118 generated by at least one oscillatory signal source. For example, the oscillatory signal source may sink or source a current, and the sinking or sourcing of current cause a voltage to form on electrodes 116, 118. In some examples, the medical device may determine the voltage across pairs of electrodes 116, 118 (e.g., bipolar voltage measurements).

The medical device may be configured to determine, based on a hypothetical location of the at least one oscillatory signal source, expected electrical signal levels at the plurality of electrodes of electrodes 116, 118. For example, the medical device may assign coordinate values as a way to guess a location of the at least one oscillatory signal source, where the assigned coordinate values define the hypothetical location of the at least one oscillatory signal source. The medical device may determine distance scalar values (e.g., G-matrix) based on a distance between each of the plurality of electrodes of electrodes 116, 118 and the hypothetical location of the oscillatory signal source. The medical device may determine an estimate of the charge of the oscillatory signal source based on the distance scalar values and the measured voltage levels (e.g., $Q'=(G^TG)^{-1}G^TV$), and determine expected voltage levels based on the estimate of the charge of the at least one oscillatory signal source (e.g., $V'=G*Q'$).

In one or more examples, the medical device may determine an error value based on the determined electrical signal levels and the expected electrical signal levels. For example, the error value is equal to the norm(V−V').

In accordance with one or more examples, the medical device may adjust the hypothetical location, and repeatedly determine the error value for each of the adjusted hypothetical locations of the at least one oscillatory signal source until the determined error value is less than or equal to a threshold value (e.g., including the example where the error value is minimized). A location of the at least one oscillatory signal source is based on a hypothetical location for the at least one oscillatory signal source for which the determined error value is less than or equal to the threshold value. For instance, the location of the oscillatory signal source is equal to the hypothetical location for the at least one oscillatory signal source for which the determined error value is reduced below a threshold value, including example where error value is minimized (e.g., minimizing the error value is one example of determining error value that is reduced below a threshold value).

The medical device may generate information indicative of the location of the at least one oscillatory signal source. As one example, the result of the operations of adjusting the hypothetical location to reduce the error value is the generation of the information indicative of the location of the at least one oscillatory signal source. The medical device may output the information indicative of the location of the at least one oscillatory signal source or utilize the information indicative of the location of the at least one oscillatory signal source to determine which electrodes 116, 118 are most proximate to the at least one oscillatory signal source.

Figure 2:
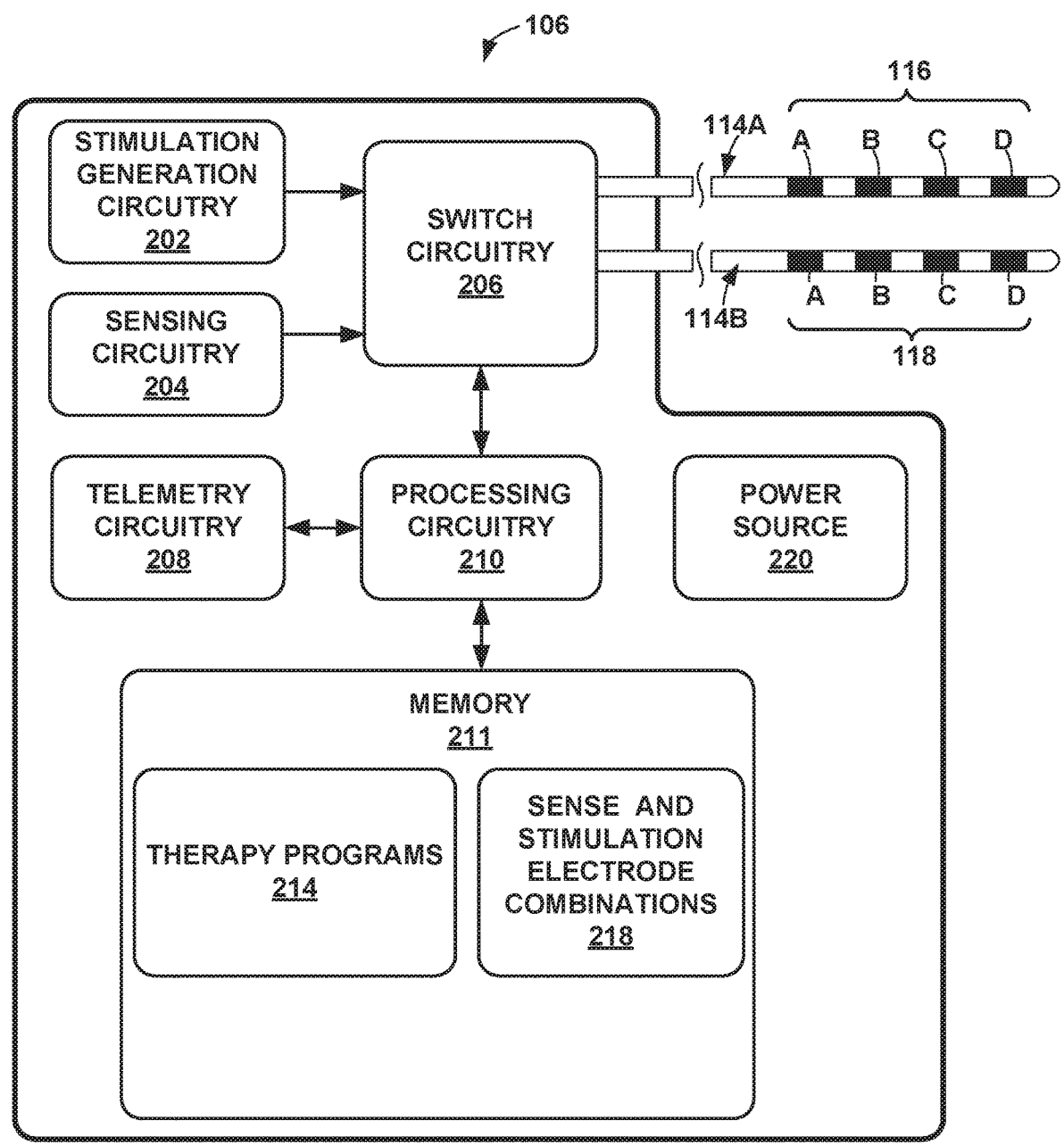
FIG. 2 is a block diagram of the example IMD of FIG. 1 for delivering adaptive DBS therapy according to an example of the techniques of the disclosure.

FIG. 2 is a block diagram of the example IMD 106 of FIG. 1 for delivering adaptive deep brain stimulation therapy. In the example shown in FIG. 2, IMD 106 includes processing circuitry 210, memory 211, stimulation generation circuitry 202, sensing circuitry 204, switch circuitry 206, telemetry circuitry 208, and power source 220. Each of these circuits may be or include electrical circuitry configured to perform the functions attributed to each respective circuit. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processing circuitry 210, cause IMD 106 to perform various functions. Memory 211 may be a storage device or other non-transitory medium.

In the example shown in FIG. 2, memory 211 stores therapy programs 214 and sense electrode combinations and associated stimulation electrode combinations 218, in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 218 stores sense electrode combinations and associated stimulation electrode combinations. As described above, in some examples, sense and stimulation electrode combinations 218 may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processing circuitry 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy.

Stimulation generation circuitry 202, under the control of processing circuitry 210, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 40 Hertz and approximately 500 Hertz, such as between approximately 90 to 170 Hertz or such as approximately 90 Hertz.
2. In the case of a voltage controlled system, Voltage Amplitude: between approximately 0.1 volts and approximately 50 volts, such as between approximately 2 volts and approximately 3 volts.
3. In the case of a current controlled system, Current Amplitude: between approximately 1 milliamps to approximately 3.5 milliamps, such as between approximately 1.0 milliamps and approximately 1.75 milliamps.
4. Pulse Width: between approximately 50 microseconds and approximately 500 microseconds, such as between approximately 50 microseconds and approximately 200 microseconds.

Accordingly, in some examples, stimulation generation circuitry 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processing circuitry 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 may control stimulation generation circuitry 202 according to therapy programs 214 stored in memory 211 to apply particular stimulation parameter values specified by one or more of programs, such as voltage amplitude or current amplitude, pulse width, and/or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processing circuitry 210 also controls switch circuitry 206 to apply the stimulation signals generated by stimulation generation circuitry 202 to selected combinations of electrodes 116, 118. In particular, switch circuitry 204 may couple stimulation signals to selected conductors within leads 114, which, in turn, deliver the stimulation signals across selected electrodes 116, 118. Switch circuitry 206 may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generation circuitry 202 is coupled to electrodes 116, 118 via switch circuitry 206 and conductors within leads 114. In some examples, however, IMD 106 does not include switch circuitry 206.

Stimulation generation circuitry 202 may be a single channel or multi-channel stimulation generator. In particular, stimulation generation circuitry 202 may be capable of delivering a single stimulation pulse, multiple stimulation pulses, or a continuous signal at a given time via a single electrode combination or multiple stimulation pulses at a given time via multiple electrode combinations. In some examples, however, stimulation generation circuitry 202 and switch circuitry 206 may be configured to deliver multiple channels on a time-interleaved basis. For example, switch circuitry 206 may serve to time divide the output of stimulation generation circuitry 202 across different electrode combinations at different times to deliver multiple programs or channels of stimulation energy to patient 112. Alternatively, stimulation generation circuitry 202 may comprise multiple voltage or current sources and sinks that are coupled to respective electrodes to drive the electrodes as cathodes or anodes. In this example, IMD 106 may not require the functionality of switch circuitry 206 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes, e.g., arranged as segments, at different perimeter locations around the perimeter of the lead at each of the locations A, B, C, and D.

As an example, one or both of leads 114 may include radially-segmented DBS arrays (rDBSA) of electrodes. In the rDBSA, as one example, there may be a first ring electrode of electrodes 116 around the perimeter of lead 114A at a first longitudinal location on lead 114A (e.g., location A). Below the first ring electrode, there may be three segmented electrodes of electrodes 116 around the perimeter of lead 114A at a second longitudinal location on lead 114A (e.g., location B). Below the three segmented electrodes, there may be another set of three segmented electrodes of electrodes 116 around the perimeter of lead 114A at a third longitudinal location of lead 114A (e.g., location C). Below the three segmented electrodes, there may be a second ring electrode of electrodes 116 around the perimeter of lead 114A (e.g., location D). Electrodes 118 may be similarly positioned along lead 114B. An example of rDBSA arrays of electrodes on a lead is described in more detail with respect to FIG. 4.

The above is one example of the rDBSA array of electrodes, and the example techniques should not be considered limited to such an example. There may be other configurations of electrodes for DBS. Moreover, the example techniques are not limited to DBS, and other electrode configurations are possible.

In one example, the electrodes 116, 118 may be electrically coupled to switch circuitry 206 via respective wires that are straight or coiled within the housing of the lead and run to a connector at the proximal end of the lead. In another example, each of the electrodes 116, 118 of the leads 114 may be electrodes deposited on a thin film. The thin film may include an electrically conductive trace for each electrode that runs the length of the thin film to a proximal end connector. The thin film may then be wrapped (e.g., a helical wrap) around an internal member to form the leads 114.

These and other constructions may be used to create a lead with a complex electrode geometry.

Although sensing circuitry 204 is incorporated into a common housing with stimulation generation circuitry 202 and processing circuitry 210 in FIG. 2, in other examples, sensing circuitry 204 may be in a separate housing from IMD 106 and may communicate with processing circuitry 210 via wired or wireless communication techniques. Example neurological brain signals include, but are not limited to, a signal generated from local field potentials (LFPs) within one or more regions of brain 120. EEG and ECoG signals are examples of local field potentials that may be measured within brain 120. LFPs, EEG and ECoG may be different measurements of the same bioelectric signals in the brain. The neurons generate the signals, and if measured at depth, it is LFP, if measured on the coretex, it is ECoG, if on the scalp, it is EEG. In general, the bioelectric signals may be formed by one or more oscillatory signal sources. The set of electrodes 116 and 118 that are most proximate to the oscillatory signal sources are good candidates to use for delivering therapy.

Telemetry circuitry 208 supports wireless communication between IMD 106 and an external programmer 104 or another computing device under the control of processing circuitry 210. Processing circuitry 210 of IMD 106 may receive, as updates to programs, values for various stimulation parameters such as magnitude and electrode combination, from programmer 104 via telemetry circuitry 208. The updates to the therapy programs may be stored within therapy programs 214 portion of memory 211. Telemetry circuitry 208 in IMD 106, as well as telemetry modules in other devices and systems described herein, such as programmer 104, may accomplish communication by radiofrequency (RF) communication techniques. In addition, telemetry circuitry 208 may communicate with external medical device programmer 104 via proximal inductive interaction of IMD 106 with programmer 104. Accordingly, telemetry circuitry 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 104. In some examples, power requirements may be small enough to allow IMD 104 to utilize patient motion and implement a kinetic energy-scavenging device to trickle charge a rechargeable battery. In other examples, traditional batteries may be used for a limited period of time.

In one example, processing circuitry 210 of IMD 106 senses, via electrodes 116, 118 interposed along leads 114 (and sensing circuitry 204), one or more bioelectric signals of brain 120 of patient 112. Further, processing circuitry 210 of IMD 106 delivers, via electrodes 116, 118 (and stimulation generation circuitry 202), electrical stimulation therapy to patient 112 based on the sensed one or more bioelectric signals of brain 120. The adaptive DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. Processing circuitry 210, via electrodes 116, 118, delivers to patient 112 adaptive DBS and may adjust one or more parameters defining the electrical stimulation based on corresponding parameters of the sensed one or more bioelectric signals of brain 120.

In some examples, processing circuitry 210 continuously measures the one or more bioelectric signals in real time. In other examples, processing circuitry 210 periodically samples the one or more bioelectric signals according to a predetermined frequency or after a predetermined amount of time. In some examples, processing circuitry 210 periodically samples the signal at a frequency of approximately 150 Hertz.

According to the techniques of the disclosure, processing circuitry 210 may be configured to determine information indicative of locations of one or more oscillatory signal sources. Processing circuitry 210 may be configured to perform such example techniques by determining an expected electrical signal level for a hypothetical location of the oscillatory signal source and determine a difference between the actual measured electrical signal levels (e.g., measured voltage levels) and expected electrical signal levels (e.g., expected voltage levels). Processing circuitry 210 may adjust the hypothetical location of the oscillatory signal source until processing circuitry 210 determines a hypothetical location of the oscillatory signal source where the difference between the measured and expected signal levels is below a threshold value (including examples where the difference is minimized).

Figure 3:
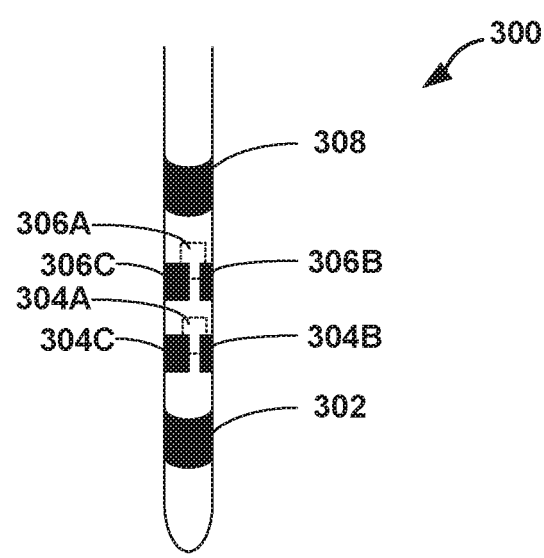
FIG. 3 is a conceptual diagram illustrating an example of a lead with segmented and ring electrodes.

As described above, processing circuitry 210 may be configured to determine electrical signal levels (e.g., voltage levels) at one or more electrodes of electrodes 116, 118 or across pairs of electrodes of electrodes 116, 118. For instance, FIG. 3 is a conceptual diagram illustrating an example of a lead 300 with segmented and ring electrodes. Lead 300 is an example of leads 114A and 114B.

The lead radius for lead 300 is approximate 0.66 mm. Lead 300 includes ring electrode 302, segmented electrodes 304A-304C, segmented electrodes 306A-306C, and ring electrode 308. The electrodes on lead 300 may be vertically (e.g., axially) spaced by a distance D (e.g., 2 mm to 3 mm). For example, assume that the z-coordinate for ring electrode 302 is 0. In this example, the z-coordinate for segment electrodes 304A-304C is D, the z-coordinate for segment electrodes 306A-306D is 2D, and the z-coordinate for ring electrode 308 is 3D.

Segmented electrodes 304A-304C may be all at the same vertical level (e.g., axial level), and segmented electrodes 306A-306C may be all at the same vertical level (e.g., axial level). In this example, the angular separation between segmented electrodes 304A-304C may be 120-degrees. Therefore, segmented electrodes 304A and 306A are on the backside of lead 300 and shown in dashed lines.

In one or more examples, processing circuitry 210 may determine the expected voltage levels on electrodes of lead 300 for a hypothetical location of the oscillatory signal source based on lead-field equations that define what the voltage should be at electrodes on lead 300 based on distance to a hypothetical location. For example, let $R_1$ to $R_N$ denote the x, y, z coordinates of electrodes of lead 300, and let $r_1$ to $r_p$ denote the x, y, z coordinates of p oscillatory signal sources.

In such examples, expected voltage at electrode $R_i$ equals a distance scalar value multiplied by a charge of oscillatory signal sources. The distance scalar value for a point charge for an oscillatory signal source is equal to: $G_{pt}(R_i, r_j) = 1/\|R_i - r_j\|$. The distance scalar value for a dipole charge for an oscillatory signal source is equal to: $G_{dp}(R_i, r_j, \Omega) = ((R_i - r_j) * u_d^T)/(\|R_i - r_j\|)^3$. For the dipole charge, $\Omega = \{d, \Theta, \varphi\}$, where d=dipole length, $\Theta$=azimuth angle, and $\varphi$=elevation angle. The variable $u_d = [\cos(\Theta)*\cos(\varphi), \sin(\Theta)*\cos(\varphi), \sin(\varphi)] \in R^{1\times 3}$ is the dipole direction (unit vector), $R_i \in R^{1\times 3}$, and $r_j \in R^{1\times 3}$.

Based on the hypothetic location of the oscillatory signal sources, the voltage levels at each of the electrodes of lead 300 can be represented as:

$$\begin{bmatrix} V(R_1) \\ \vdots \\ V(R_N) \end{bmatrix} = \begin{bmatrix} G(R_1, r_1) & \cdots & G(R_1, r_P) \\ \vdots & \cdots & \vdots \\ G(R_N, r_1) & \cdots & G(R_N, r_P) \end{bmatrix} * \begin{bmatrix} Q_1 \\ \vdots \\ Q_P \end{bmatrix} + e$$

In the above equation, $V(R_1)$ to $V(R_N)$ represent the actual measured voltages at electrodes of lead 300 (e.g., mono-polar measured voltages with respect to ground). However, as described in more detail below, rather than mono-polar voltage level measurements, processing circuitry 210 may be configured to receive bipolar voltage level measurements (e.g., voltage levels between two electrodes on lead 114A or between two electrodes on lead 114B). For ease, the following describes examples where mono-polar voltage measurements are available, and this disclosure further below describes examples where bipolar voltage measurements are available.

The G-matrix represents the distance scalar values for each electrode $R_1$ to $R_N$ for each oscillatory signal source $r_1$ to $r_p$. $Q_1$ to $Q_p$ represent the charge for each oscillatory signal source. The variable e indicates the error value between expected voltage levels and the measured voltage levels.

For instance, $V = G*Q + e$, where $E(e) = 0$, $\mathrm{cov}(e) = I\sigma^2$. In this equation, e represents the error in the model GQ and measured Voltage. The error is assumed to have 0 mean and constant variance $\sigma^2$. As described above, the charge of the oscillatory signal sources is unknown. The error value (e) is based on the difference between the actual measured voltage level (e.g., V) and the expected voltage level (e.g., V'). For instance, error=norm(V−V'). The expected voltage level, V', is based on the distance scalar values and an expected charge value (Q') of the oscillatory signal sources. For instance, V'=G*Q', and therefore, error=norm(V−G*Q'). The expected charge value $Q' = (G^T G)^{-1} G^T V$.

In one or more examples, processing circuitry 210 may adjust the hypothetical location to minimize the error value. Minimizing the error value may be the same as maximizing the fit value in least square formulation. The fit value is equal to −log 10(error value). In the least square formulation, the solution to V=G*Q+e, for unknown Q and known G is a least squares problem: $Q_{lsq} = \min_Q \|e\|^2 = \min_Q \|V - GQ\|^2$.

However, in some examples, processing circuitry 210 may not determine voltage at the electrodes (e.g., not determine $V(R_i)$). Rather, processing circuitry 210 may measure a bipolar montage represented by C*V. For example, C*V can be represented as follows:

$$C = \begin{bmatrix} 1 & -1 & 0 & 0 \\ 1 & 0 & -1 & 0 \\ 1 & 0 & 0 & -1 \\ 0 & 1 & -1 & 0 \\ 0 & 1 & 0 & -1 \\ 0 & 0 & 1 & -1 \end{bmatrix} * \begin{bmatrix} V(R_1) \\ V(R_2) \\ V(R_3) \\ V(R_4) \end{bmatrix} = \begin{bmatrix} V(R_1) - V(R_2) \\ V(R_1) - V(R_3) \\ V(R_1) - V(R_4) \\ V(R_2) - V(R_3) \\ V(R_2) - V(R_4) \\ V(R_3) - V(R_4) \end{bmatrix}$$

There may be various electrodes of lead 300 across which processing circuitry 210 may determine the voltage difference. In some examples, due to impedance mismatch between segmented and ring electrodes, processing circuitry 210 may not determine the voltage across a segmented electrode and a ring electrode. However, in some examples, processing circuitry 210 may couple segmented electrodes of the same vertical (e.g., axial) level together to form an effective ring electrode. Processing circuitry 210 may determine the voltage across an effective ring electrode and an actual ring electrode.

In general, it may be possible for processing circuitry 210 to determine the voltage across certain pairs of electrodes, and then also, from the determined voltages, determine voltages across other pairs of electrodes. Determining voltage levels across a set of electrode pairs is referred to as a montage of voltage measurements. In some examples, it may be possible for processing circuitry 210 to measure a reference montage of voltage measurements, and from the reference montage of voltage measurements, determine the voltage measurements across a different set of electrode pairs.

For example, in the following, x denotes the measured signals. Also, in the following V0 refers to the voltage at electrode 302, V1 refers to the voltage when electrodes 304A-304C are coupled together to form a first effective ring electrode, where electrodes 304A-304C are at the same axial level, V2 refers to the voltage when electrodes 306A-306C are coupled together to form a second effective ring electrode, where electrodes 306A-306C are at the same axial level, and V3 refers to the voltage at electrode 308. V1a, V1b, and V1c refer to the respective voltages at electrodes 304A-304C when electrodes 304A-304C are not coupled together, and V2a, V2b, and V2c refer to the respective voltages at electrodes 306A-306C when electrodes 306A-306C are not coupled together.

Again, V0, V1, V2, V3, V1a-V1c, and V2a-V2c represent mono-sensed voltages (e.g., mono-polar voltage level measurements with respect to ground). However, sensing circuitry 204 may measure voltages between electrodes (e.g., bipolar voltage measurements), rather than with respect to ground. Accordingly, in the following, processing circuitry 210 may determine (e.g., receive) the "x" values based on information from sensing circuitry 204, where the "x" values represent different bipolar measurements.

$x1 = V0 - V1$ $x2 = V2 - V1$ $x3 = V2 - V3$ $x4 = V0 - V3$ $x5 = V1a - V1b$ $x6 = V1c - V1b$ $x7 = V1a - V2a$ $x8=V2a-V2b$ $x9=V2c-V2b$ $x10=V2c-V1c$

While the voltage measurement montage of x1-x10 may be the values that processing circuitry 210 determines, processing circuitry 210 may compute other voltage measurement montages based on the x1-x10 voltages. For instance, in the following, the "y" values represent the desired voltage values that are used to determine the voltage levels for determining location of the oscillatory signal sources.

y1=V0-V1, which is the same as x1
y2=V0-V2, which is the same as x1-x2
y3=V0-V3, which is the same as x4
y4=V1a-V1b, which is the same as x5
y5=V1a-V1c, which is the same as x5-x6
y6=V1a-V2a, which is the same as x7
y7=V1a-V2b, which is the same as x7+x8
y8=V1a-V2c, which is the same as x7+x8-x9

Lead 300 is used as an example, and as described above, lead 300 is an example of leads 114A and 114B. In some examples, for parallel sensing of the voltage levels, processing circuitry 210 may cause the segmented electrodes of leads 114A and 114B, that are at the same axial level, to be coupled together to form the effective ring electrodes, and perform the voltage measurements between the ring electrodes, between the ring electrodes and the effective ring electrodes, and between the effective ring electrodes. Then, processing circuitry 210 may cause the segmented electrodes of leads 114A and 114B to not be coupled to each other and perform the voltage measurements between the segmented electrodes of the same axial level.

As described above, the bipolar montage can be represented as C*V. For instance, as noted above:

$$C = \begin{bmatrix} 1 & -1 & 0 & 0 \\ 1 & 0 & -1 & 0 \\ 1 & 0 & 0 & -1 \\ 0 & 1 & -1 & 0 \\ 0 & 1 & 0 & -1 \\ 0 & 0 & 1 & -1 \end{bmatrix} * \begin{bmatrix} V(R_1) \\ V(R_2) \\ V(R_3) \\ V(R_4) \end{bmatrix} = \begin{bmatrix} V(R_1) - V(R_2) \\ V(R_1) - V(R_3) \\ V(R_1) - V(R_4) \\ V(R_2) - V(R_3) \\ V(R_2) - V(R_4) \\ V(R_3) - V(R_4) \end{bmatrix}$$

Because processing circuitry 210 may determine bipolar montages, in some examples, processing circuitry 210 may utilize the bipolar montage of voltages (e.g., C*V) to perform the examples techniques described in this disclosure, as part of the generalized least squares algorithm.

For instance, as described above, V=G*Q+e. Therefore, C*V=C*G*Q+C*e. In this example, C*V represent the actual voltage measurements that processing circuitry 210 determines. Assuming that Y=C*V, X=C*G, and e_bipolar is C*e, then C*V=C*G*Q+C*e can be rewritten as Y=X*Q+e_bipolar. Similar to above, E(e_bipolar)=0, and cov(e_bipolar)=C*C$^T$*σ$^2$. Similar to above, e_bipolar is the error under the montage transformation C.

The error value, e_bipolar, is based on the difference between the actual measured bipolar voltage levels (e.g., Y or C*V) and the expected voltage level (e.g., Y' or C*V'). For instance, the error value for e_bipolar is equal to norm(Y-Y'). The expected bipolar voltage level, Y', is based on the distance scalar values and the expected charge value (Q'_bipolar). In this example, Q'_bipolar is the estimate of the charge of the oscillatory signal source where the voltage level measurements are bipolar. For instance, Y'=X*Q'_bipolar, where X=C*G, and therefore, e_bipolar=norm(Y-X*Q'_bipolar). The expected charge value for Q'_bipolar is equal to $(X^TX)^{-1}X^TY$, where X is equal to C*G and Y is equal to C*V. The fit value for the least squares technique may be represented as fit=-log 10(e_bipolar).

The bipolar voltage measurements may be time-varying voltage measurements (e.g., the voltage level is time-varying) because the signal from the oscillatory signal source is time-varying (e.g., oscillating). Therefore, an instantaneous measurement of the voltage may not accurately reflect the time-varying nature of the voltage level. Accordingly, in some examples, processing circuitry 210 may determine a root-mean-square (RMS) voltage level based on the bipolar voltage measurements and perform the example techniques described in this disclosure based on the RMS voltage level.

For example, Y=C*V and X=C*G. Therefore, RMS(Y)=RMS(X*Q+e_bipolar). Assume that $Y_r$=RMS(Y) and $X_r$=|X|. Accordingly, $Y_r$=$X_r$*$Q_r$+e_bipolar$_r$. The RMS error value, e_bipolar$_r$, is based on the difference between the actual measured RMS bipolar voltage levels (e.g., $Y_r$ or C*$V_r$) and the expected RMS voltage level (e.g., $Y_r$' or C*$V_r$'). For instance, the error value for e_bipolar$_r$ is equal to norm($Y_r$-$Y_r$'). The expected RMS bipolar voltage level, $Y_r$', is based on the distance scalar values and the expected charge value (Q'_bipolar$_r$). In this example, Q'_bipolar$_r$ is the estimate of the charge of the oscillatory signal source where the voltage level measurements are bipolar RMS measurements. For instance, $Y_r$'=X*Q'_bipolar$_r$, where $X_r$=|C*G|, and therefore, e_bipolar$_r$=norm(Y-$X_r$*Q'_bipolar$_r$). The expected charge value for Q'_bipolar$_r$ is equal to $(X_r^TX_r)^{-1}X_r^TY_r$, where $X_r$ is equal to |X|, X is equal to C*G and $Y_r$ is equal to RMS(Y), and Y is equal to C*V. The fit value for the least squares technique may be represented as fit=-log 10(e_bipolar$_r$). In some examples, RMS value can be tailored to a specific oscillatory frequency band of interest (e.g. beta oscillations) by filtering the LFP data in the band of interest and then calculating RMS or calculating the spectral power of the LFP in the band of interest.

The example techniques described in this disclosure may be applicable where mono-polar voltage measurements (e.g., V) for electrodes are used, bipolar voltage measurements (e.g., Y where Y=C*V) for electrodes are used, and examples where RMS voltage levels are used (e.g., RMS(V) or RMS(Y)). For example, processing circuitry 210 may determine electrical signal levels at or across a plurality of electrodes generated by at least one oscillatory signal source (e.g., determine V, Y, RMS(V) or RMS(Y)). Processing circuitry 210 may determine, based on a hypothetical location of the at least one oscillatory signal source, expected electrical signal levels at the plurality of electrodes. For example, processing circuitry 210 may determine V', where V' is equal to G*Q', may determine Y', where Y' is equal to X*Q'_bipolar and where X is equal to C*G, or may determine RMS(Y'), where RMS(Y') is equal to $Y_r$', which is equal to X*Q'_bipolar, where X is equal to C*G, as a few examples.

Processing circuitry 210 may determine an error value based on the determined electrical signal levels and the expected electrical signal levels. For example, processing circuitry 210 may determine e (e.g., norm(V-V'), may determine e_bipolar (e.g., norm(Y-Y'), or may determine e_bipolar$_r$ (e.g., norm($Y_r$,31 $Y_r$'), as a few examples.

Processing circuitry 210 may adjust the hypothetical location, and repeatedly determine the error value (e.g., e, e_biploar, or e_bipolar$_r$) for each of the adjusted hypothetical locations of the at least one oscillatory signal source until the determined error value is less than or equal to a threshold value (e.g., including the example where the error value is minimized). A location of the at least one oscillatory signal source is based on a hypothetical location for the at least one oscillatory signal source for which the determined error value is less than or equal to the threshold value. Processing circuitry 210 may generate information indicative of the location of the at least one oscillatory signal source.

As described above, minimizing the error value is equivalent to maximizing the fit value. Accordingly, for cylindrical coordinates for the location of the oscillatory signal source (e.g., r, Θ, z), processing circuitry 210 may perform the operations to maximize the fit value. For example, processing circuitry 210 may perform one of the following operations based on whether mono-polar, bipolar, or RMS voltage measurements are determined. The techniques may be extended to examples where RMS mono-polar voltage measurements are available.

argmax{-log 10(norm(V-G(Ω)*Q'))}, for mono-polar voltage level measurements;
argmax{-log 10(norm(Y-X(Ω)*Q_bipolar'))}, for bipolar voltage level measurements; or
argmax{-log 10(norm(Y$_r$-X$_r$(Ω)*Q_bipolar$_r$'))}, for RMS bipolar voltage level measurement.

In the above equation, because the coordinates are cylindrical, for a point charge of an oscillatory signal source:

$$\Omega = \begin{bmatrix} r \in R^3 \\ \theta \in [0, 2\pi] \\ z \in R^3 \end{bmatrix}$$

For a dipole charge of the oscillatory signal source, for the cylindrical coordinates:

$$\Omega = \begin{bmatrix} r \in R^3 \\ \theta \in [0, 2\pi] \\ z \in R^3 \\ \vartheta_{dp} \in [0, 2\pi] \\ \varphi_{dp} \in [-\pi, \pi] \end{bmatrix}$$

Figure 4:
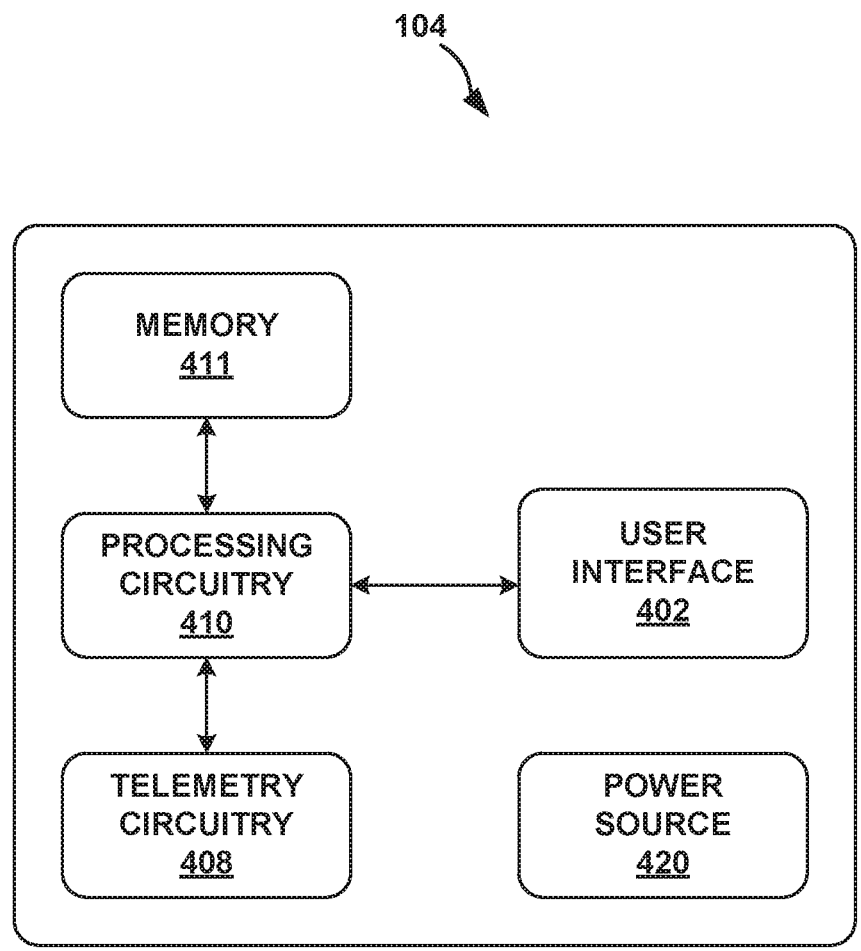
FIG. 4 is a block diagram of the external programmer of FIG. 1 for controlling delivery of adaptive DBS therapy according to an example of the techniques of the disclosure.

FIG. 4 is a block diagram of the external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 4, programmer 104 may include processing circuitry 410, memory 411, user interface 402, telemetry circuitry 408, and power source 420. Memory 411 may store instructions that, when executed by processing circuitry 410, cause processing circuitry 410 and external programmer 104 to provide the functionality ascribed to external programmer 104 throughout this disclosure. Each of these components, or modules, may include electrical circuitry that is configured to perform some or all of the functionality described herein. For example, processing circuitry 410 may include processing circuitry configured to perform the processes discussed with respect to processing circuitry 410.

In general, programmer 104 comprises any suitable arrangement of hardware, alone or in combination with software and/or firmware, to perform the techniques attributed to programmer 104, and processing circuitry 410, user interface 402, and telemetry circuitry 408 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 411, such as RAM, ROM, PROM, EPROM, EEPROM, flash memory, a hard disk, a CD-ROM, comprising executable instructions for causing the one or more processors to perform the actions attributed to them. Moreover, although processing circuitry 410 and telemetry circuitry 408 are described as separate modules, in some examples, processing circuitry 410 and telemetry circuitry 408 may be functionally integrated with one another. In some examples, processing circuitry 410 and telemetry circuitry 408 correspond to individual hardware units, such as ASICs, DSPs, FPGAs, or other hardware units.

Memory 411 (e.g., a storage device) may store instructions that, when executed by processing circuitry 410, cause processing circuitry 410 and programmer 104 to provide the functionality ascribed to programmer 104 throughout this disclosure. For example, memory 411 may include instructions that cause processing circuitry 410 to obtain a parameter set from memory or receive a user input and send a corresponding command to IMD 106, or instructions for any other functionality. In addition, memory 411 may include a plurality of programs, where each program includes a parameter set that defines stimulation therapy.

User interface 402 may include a button or keypad, lights, a speaker for voice commands, a display, such as a liquid crystal (LCD), light-emitting diode (LED), or organic light-emitting diode (OLED). In some examples the display may be a touch screen. User interface 402 may be configured to display any information related to the delivery of stimulation therapy, identified patient behaviors, sensed patient parameter values, patient behavior criteria, or any other such information. User interface 402 may also receive user input. The input may be, for example, in the form of pressing a button on a keypad or selecting an icon from a touch screen.

Telemetry circuitry 408 may support wireless communication between IMD 106 and programmer 104 under the control of processing circuitry 410. Telemetry circuitry 408 may also be configured to communicate with another computing device via wireless communication techniques, or direct communication through a wired connection. In some examples, telemetry circuitry 408 provides wireless communication via an RF or proximal inductive medium. In some examples, telemetry circuitry 408 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection.

In some examples, processing circuitry 410 of external programmer 104 defines the parameters of electrical stimulation therapy, stored in memory 411, for delivering adaptive DBS to patient 112. In one example, processing circuitry 410 of external programmer 104, via telemetry circuitry 408, issues commands to IMD 106 causing IMD 106 to deliver electrical stimulation therapy via electrodes 116, 118 via leads 114.

In one or more examples, programmer 104 may be configured to perform one or more of the example techniques described in this disclosure. For instance, processing circuitry 410 may be configured to perform any of the example operations described above with respect to processing circuitry 210. For example, as described above, IMD 106 includes sensing circuitry 204 to receive the bioelectric signals from one or more electrodes, and stimulation generation circuitry 202 to deliver the electrical stimulation having the final therapy parameter value. In some examples, telemetry circuitry 408 may be configured to receive information of the bioelectric signals received by sensing circuitry 204 (e.g., telemetry circuitry 208 of IMD 106 may output information of the bioelectric signal to telemetry circuitry 408 of programmer 104). Processing circuitry 410 may perform the example operations described above with respect to processing circuitry 210. In some examples, programmer 104 may perform some of the operations and IMD 106 may perform some of the operations.

Figure 5:
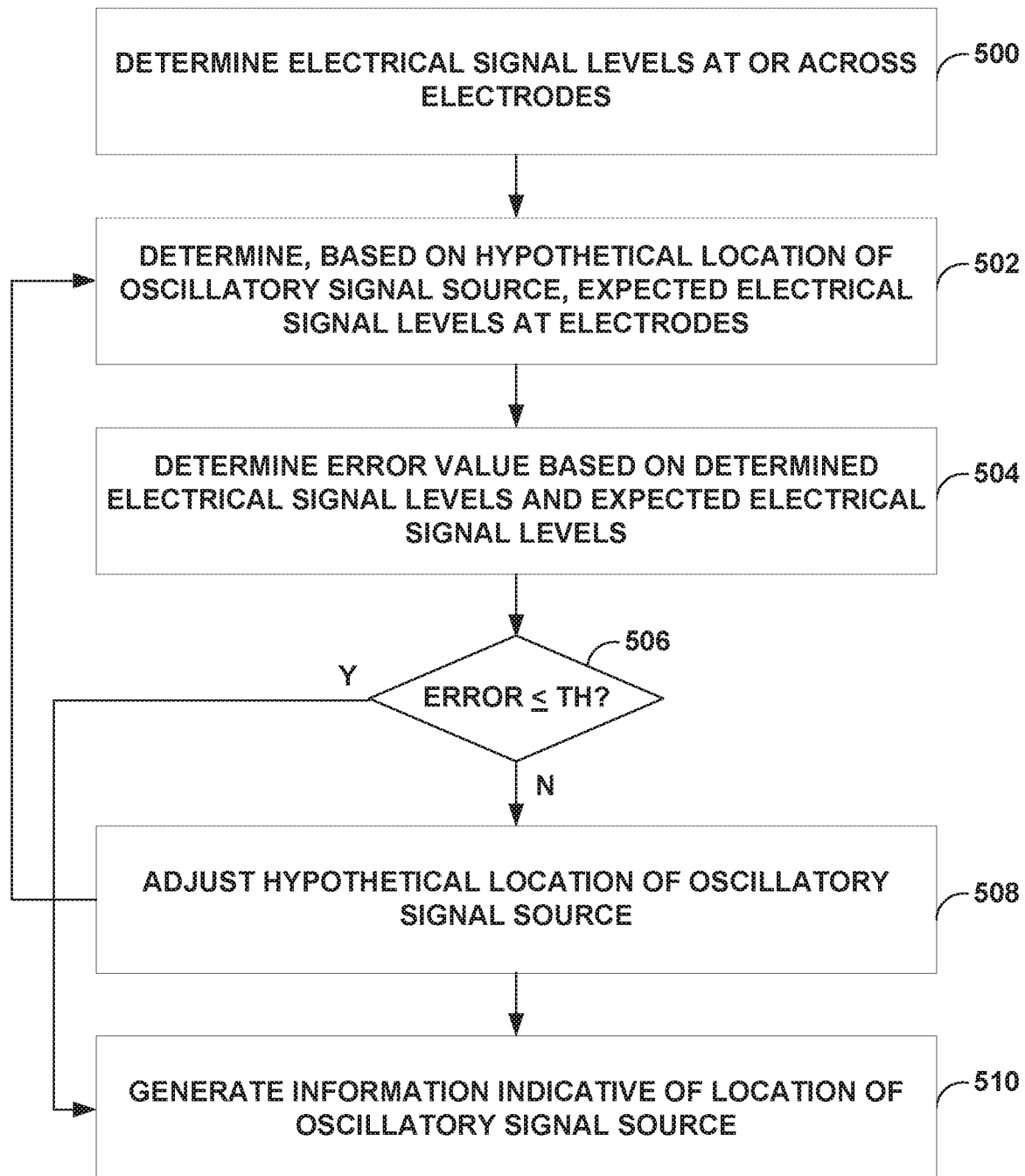
FIG. 5 is a flowchart illustrating an example operation in accordance with techniques of the disclosure.

FIG. 5 is a flowchart illustrating an example operation in accordance with techniques of the disclosure. For ease of description, the example of FIG. 5 is described with respect to processing circuitry 210 of IMD 106, but may be performed by processing circuitry 410 of programmer 104 or possibly a combination of both.

Processing circuitry 210 may be configured to determine electrical signal levels at or across a plurality of electrodes (500). For instance, processing circuitry 210 may cause sensing circuitry 204 to perform a plurality of voltage measurements. Sensing circuitry 204 may store the voltage measurements in memory 211 (or some other memory such as local memory of processing circuitry 210). Processing circuitry 210 may retrieve the voltage measurements from memory (e.g., memory 211, memory of processing circuitry 210 including registers, or some other memory).

For example, the electrical signal may be generated by at least one oscillatory signal source in brain 120. In some examples, sensing circuitry 204 may measure mono-polar voltage measurements on electrodes 116, 118 of leads 114A and 114B, where the mono-polar voltage measurements are made with respect to ground. In some examples, sensing circuitry 204 may measure bipolar voltage measurements across electrodes 116, 118. For example, sensing circuitry 204 may measure differential voltages (e.g., bipolar voltages) between two segmented electrodes. As another example, processing circuitry 210 may couple electrodes on a same axial level with one another to form an effective ring electrode and determine a differential voltage (e.g., bipolar voltage) between the effective ring electrode and another ring electrode. Examples of the differential voltages (e.g., bipolar voltages) that sensing circuitry 204 may measure are the x1-x10 montage of voltages described above. Moreover, the determined electrical signals may be RMS voltage levels, in some examples.

In some examples, sensing circuitry 204 may output the measured voltages (e.g., at or across the electrodes) to processing circuitry 210, and in such examples, processing circuitry 210 may determine the electrical signal levels (e.g., voltage levels) based on the received measured voltages. In some examples, the desired voltage levels and the measured voltage levels may be different. Examples of the desired voltage levels may be the y1-y8 voltage levels described above. In such examples, processing circuitry 210 may determine the electrical signal levels (e.g., desired voltage levels) based on computations performed on the received measured voltages to generate the desired voltage levels (e.g., perform operations on x1-x10 to generate the y1-y8 values).

Processing circuitry 210 may determine, based on a hypothetical location of the at least one oscillatory signal source, expected signal levels at the plurality of electrodes (502). For example, processing circuitry 210 may assign coordinates (e.g., Cartesian or cylindrical) as a staring hypothetical location of the at least one oscillatory signal source. The actual oscillatory signal source may not be located at the hypothetical location, and the hypothetical location is a guess of the location of the oscillatory signal source.

There may be various ways in which to determine the expected signal levels. For instance, processing circuitry 210 may determine the expected electrical signal levels based on lead-field equations (also called electrical field equations) that define relationship between the expected electrical signal levels and the hypothetical location. For instance, the lead-field equations define a plurality of distance scalar values (e.g., G-matrix) based on coordinates of the electrodes and coordinates of the hypothetical location. For example, the distance scalar values may be: $G_{pt}(R_i, r_j)=1/\|R_i-r_j\|$ for a point charge oscillatory signal source, and $G_{dp}(R_i, r_j, \Omega)=((R_i-r_j)*u_d^T)/(\|R_i-r_j\|)^3$ for a dipole oscillatory signal source, as described above.

The expected voltage levels equal $G*Q'$ for mono-polar voltage measurements, $C*G*Q'\_bipolar$ for bipolar voltage measurements, and $C*G*Q'\_bipolar_r$ for RMS bipolar measurements, as described above. For instance, processing circuitry 210 may determine an excepted charge value (e.g., Q', Q'_bipolar, or Q'_bipolar$_r$, as appropriate) for the oscillatory signal source based on the distance scalar values and the measured voltage levels (e.g., $Q'=(G^TG)^{-1}G^TV$, Q'_bipolar=$(X^TX)^{-1}X^TY$, where X is equal to $C*G$ and Y is equal to $C*V$, or Q'_bipolar$_r$=$(X_r^TX_r)^{-1}X_r^TY_r$, where $X_r$ is equal to |X|, X is equal to $C*G$, and $Y_r$ is equal to RMS(Y), and Y is equal to $C*V$). Processing circuitry 210 may multiply the expected charge value and the measured voltage levels to determine the plurality of expected voltage values (e.g., V', Y', or Y'$_r$).

Processing circuitry 210 may determine an error value based on the determined electrical signal levels and the expected electrical signals (504). For example, processing circuitry 210 may determine the error value based on a difference between the measured voltage levels and expected voltage levels (e.g., e, e_bipolar, or e_bipolar$_r$). As one example, e=norm(V−V'), e_bipolar=norm(Y−Y'), and e_bipolar$_r$=norm(Y$_r$−Y$_r$').

Processing circuitry 210 may determine whether the error value is less than or equal to a threshold value (506). One example of determining whether the error value is less than or equal to a threshold value is determining whether the error value is minimized. If the error value is not less than or equal to the threshold value (N of 506), processing circuitry 210 may adjust the hypothetical location of the at least one oscillatory signal source (508), and determine the expected electrical signal levels for the adjusted location (502) and the error value between the determined electrical signal levels and the expected electrical signal levels for the adjusted location (504).

In this way, processing circuitry 210 may repeatedly adjust the hypothetical location of the oscillatory signal source, and repeatedly determine the error value for each of the adjusted hypothetical locations of the at least one oscillatory signal source until the determined error value is less than or equal to a threshold value (e.g., Y of 506). For example, a location of the at least one oscillatory signal source is based on a hypothetical location for the at least one oscillatory signal source for which the determined error value is less than or equal to the threshold value (e.g., including examples where the error value is minimized). In some examples, processing circuitry 210 may determine that the location of the at least one oscillatory signal source is equal to the hypothetical location for the at least one oscillatory signal source for which the determined error value is less than or equal to the threshold value.

Processing circuitry 210 may generate information indicative of the location of the oscillatory signal source (510). For example, the information indicative of the location of the oscillatory signal source may be the result of the repeated adjustment of the hypothetical location until processing circuitry 210 determined the hypothetical location of the oscillatory signal source. In some examples, processing circuitry 210 may further determine which ones of electrodes 116, 118 are most proximate to the oscillatory signal source and generate information indicating which electrodes 116, 118 are most proximate.

For example, processing circuitry 210 may output information indicative of which electrodes 116, 118 are most proximate, and then these electrodes may be selected as the electrodes with which to deliver therapy. Accordingly, processing circuitry 210 may be configured to cause therapy to be delivered from the electrodes 116, 118 that are most proximate to the oscillatory signal source.

In general, processing circuitry 210 may be configured to deliver therapy using electrodes selected based on location of the oscillatory signal source. For example, processing circuitry 210 may be configured to deliver therapy using electrodes most proximate to the oscillatory signal source, but the example techniques are not so limited. In some examples, various other factors such as capabilities of IMD 106, electrical fields, etc. may together be used, in addition to location of the oscillatory signal source, to determine which electrodes to use for therapy delivery. Moreover, processing circuitry 210 may be configured to determine therapy parameters based on location of oscillator signal source. For example, based on the determined location, processing circuitry 210 may determine amplitude, frequency, and which electrodes to use so as to create a therapy field that encompasses the oscillator signal source.

The following examples are example systems, devices, and methods described herein.

Example 1. A method comprising determining electrical signal levels at or across a plurality of electrodes implanted in tissue of a patient, wherein the electrical signal levels are generated by at least one oscillatory signal source in the tissue of the patient, determining, based on a hypothetical location of the at least one oscillatory signal source, expected electrical signal levels at the plurality of electrodes, determining an error value based on the determined electrical signal levels and the expected electrical signal levels, repeatedly adjusting the hypothetical location, and repeatedly determining the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value, and generating information indicative of the location of the at least one oscillatory signal source.

Example 2. The method of example 1, wherein the location of the at least one oscillatory signal source is equal to the hypothetical location for the at least one oscillatory signal source for which the determined error value is less than or equal to the threshold value.

Example 3. The method of any of examples 1 and 2, further comprising determining which electrodes of the plurality of electrodes are most proximal to the at least one oscillatory signal source based on the location of the at least one oscillatory signal source and generating information indicative of the determined electrodes.

Example 4. The method of example 3, further comprising causing the determined electrodes to deliver electrical stimulation.

Example 5. The method of any of examples 1-4, wherein determining, based on the hypothetical location of the at least one oscillatory signal source, expected electrical signal levels at the plurality of electrodes comprises determining the expected electrical signal levels based on lead-field equations that define one or more relationships between the expected electrical signal levels and the hypothetical location.

Example 6. The method of example 5, wherein the lead-field equations define a plurality of distance scalar values based on coordinates of the electrodes and coordinates of the hypothetical location, wherein the determined electrical signals comprise a plurality of measured voltage levels, and wherein determining the error value based on the determined electrical signal levels and the expected electrical signal levels comprises determining an expected charge value for the at least one oscillatory signal source based on the distance scalar values and the measured voltage levels, multiplying the expected charge value and the measured voltage levels to determine a plurality of expected voltage values, and determining the error value based on a difference between the measured voltage levels and expected voltage levels.

Example 7. The method of any of examples 1-6, wherein determining the electrical signal levels at or across the plurality of electrodes generated by the at least one oscillatory signal source comprises determining a differential voltage between two segmented electrodes of the plurality of electrodes.

Example 8. The method of any of examples 1-7, wherein determining the electrical signal levels at or across the plurality of electrodes generated by the at least one oscillatory signal source comprises coupling a plurality of segmented electrodes that are at the same axial level together to form an effective ring electrode and determining a differential voltage between the effective ring electrode and another ring electrode.

Example 9. The method of any of examples 1-8, wherein repeatedly determining the error value for each of the adjusted hypothetical locations of the at least one oscillatory signal source until the determined error value is less than or equal to the threshold value comprises repeatedly determining the error value for each of the adjusted hypothetical locations of the at least one oscillatory signal source until the determined error value is minimized.

Example 10. A medical device comprising a memory configured to store information indicative of electrical signal levels at or across a plurality of electrodes implanted in tissue of a patient and processing circuitry configured to determine the electrical signal levels based on the stored information, determine, based on a hypothetical location of the at least one oscillatory signal source, expected electrical signal levels at the plurality of electrodes, determine an error value based on the determined electrical signal levels and the expected electrical signal levels, repeatedly adjust the hypothetical location, and repeatedly determine the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value, and generate information indicative of the location of the at least one oscillatory signal source.

Example 11. The medical device of example 10, wherein the medical device comprises an implantable medical device.

Example 12. The medical device of example 10, wherein the medical device comprises a programmer.

Example 13. The medical device of any of examples 10-12, wherein the location of the at least one oscillatory signal source is equal to the hypothetical location for the at least one oscillatory signal source for which the determined error value is less than or equal to the threshold value.

Example 14. The medical device of any of examples 10-13, wherein the processing circuitry is configured to determine which electrodes of the plurality of electrodes are most proximal to the at least one oscillatory signal source based on the location of the at least one oscillatory signal source and generate information indicative of the determined electrodes.

Example 15. The medical device of any of examples 10-14, wherein the processing circuitry is configured to cause the determined electrodes to deliver electrical stimulation.

Example 16. The medical device of any of examples 10-15, wherein to determine, based on the hypothetical location of the at least one oscillatory signal source, expected electrical signal levels at the plurality of electrodes, the processing circuitry is configured to determine the expected electrical signal levels based on lead-field equations that define one or more relationships between the expected electrical signal levels and the hypothetical location.

Example 17. The medical device of example 16, wherein the lead-field equations define a plurality of distance scalar values based on coordinates of the electrodes and coordinates of the hypothetical location, wherein the determined electrical signals comprise a plurality of measured voltage levels, and wherein to determine the error value based on the determined electrical signal levels and the expected electrical signal levels, the processing circuitry is configured to determine an expected charge value for the at least one oscillatory signal source based on the distance scalar values and the measured voltage levels, multiply the expected charge value and the measured voltage levels to determine a plurality of expected voltage values, and determine the error value based on a difference between the measured voltage levels and expected voltage levels.

Example 18. The medical device of any of examples 10-17, wherein to determine the electrical signal levels at or across the plurality of electrodes generated by the at least one oscillatory signal source, the processing circuitry is configured to determine a differential voltage between two segmented electrodes of the plurality of electrodes.

Example 19. The medical device of any of examples 10-18, wherein to determine the electrical signal levels at or across the plurality of electrodes generated by the at least one oscillatory signal source, the processing circuitry is configured to cause coupling of a plurality of segmented electrodes that are at the same axial level together to form an effective ring electrode and determine of a differential voltage between the effective ring electrode and another ring electrode.

Example 20. The medical device of any of examples 10-19, wherein to repeatedly determine the error value for each of the adjusted hypothetical locations of the at least one oscillatory signal source until the determined error value is less than or equal to the threshold value, the processing circuitry is configured to repeatedly determine the error value for each of the adjusted hypothetical locations of the at least one oscillatory signal source until the determined error value is minimized.

Example 21. A system comprising one or more leads comprising electrodes implanted in tissue of a patient, a sensing circuitry configured to sense electrical signal levels at or across a plurality of the electrodes, and processing circuitry configured to determine the electrical signal levels based on information indicative of the sensed electrical signals from the sensing circuitry, determine, based on a hypothetical location of the at least one oscillatory signal source, expected electrical signal levels at the plurality of electrodes, determine an error value based on the determined electrical signal levels and the expected electrical signal levels, repeatedly adjust the hypothetical location, and repeatedly determine the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value, and generate information indicative of the location of the at least one oscillatory signal source.

Example 22. The system of example 21, wherein the system comprises an implantable medical device, wherein the implantable medical device comprises the sensing circuitry and the processing circuitry.

Example 23. The system of example 21, wherein the system comprises an implantable medical device and a programmer, wherein the implantable medical device comprises the sensing circuitry and the programmer comprises the processing circuitry.

Example 24. A computer-readable storage medium comprising instructions stored thereon that when executed one or more processors of a medical device to determine electrical signal levels at or across a plurality of electrodes implanted in tissue of a patient, wherein the electrical signal levels are generated by at least one oscillatory signal source in the tissue of the patient, determine, based on a hypothetical location of the at least one oscillatory signal source, expected electrical signal levels at the plurality of electrodes, determine an error value based on the determined electrical signal levels and the expected electrical signal levels, repeatedly adjust the hypothetical location, and repeatedly determine the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value, and generate information indicative of the location of the at least one oscillatory signal source.

Example 25. The computer-readable storage medium of example 24, further comprising instructions that cause the one or more processors to determine which electrodes of the plurality of electrodes are most proximal to the at least one oscillatory signal source based on the location of the at least one oscillatory signal source and generate information indicative of the determined electrodes.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
    determining electrical signal levels at or across a plurality of electrodes implanted in a brain of a patient, wherein the electrical signal levels are generated by at least one oscillatory signal source in the brain of the patient;
    determining, based on a hypothetical location of the at least one oscillatory signal source, expected electrical signal levels at the plurality of electrodes;
    determining an error value based on the determined electrical signal levels and the expected electrical signal levels;
    repeatedly adjusting the hypothetical location, and repeatedly determining the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value;
    generating information indicative of the location of the at least one oscillatory signal source; and
    causing delivery of an electrical stimulation signal based on the information indicative of the location of the oscillatory signal source.

2. The method of claim 1, wherein the location of the at least one oscillatory signal source is equal to the hypothetical location for the at least one oscillatory signal source for which the determined error value is less than or equal to the threshold value.

3. The method of claim 1, further comprising:
    determining which electrodes of the plurality of electrodes are most proximal to the at least one oscillatory signal source based on the location of the at least one oscillatory signal source; and
    generating information indicative of the determined electrodes.

4. The method of claim 3, wherein causing delivery of the electrical stimulation signal comprises causing the determined electrodes to deliver the electrical stimulation signal.

5. The method of claim 1, wherein determining, based on the hypothetical location of the at least one oscillatory signal source, expected electrical signal levels at the plurality of electrodes comprises determining the expected electrical signal levels based on lead-field equations that define one or more relationships between the expected electrical signal levels and the hypothetical location.

6. The method of claim 5, wherein the lead-field equations define a plurality of distance scalar values based on coordinates of the electrodes and coordinates of the hypothetical location, wherein the determined electrical signals comprise a plurality of measured voltage levels, and wherein determining the error value based on the determined electrical signal levels and the expected electrical signal levels comprises:
    determining an expected charge value for the at least one oscillatory signal source based on the distance scalar values and the measured voltage levels;
    multiplying the expected charge value and the measured voltage levels to determine a plurality of expected voltage values; and
    determining the error value based on a difference between the measured voltage levels and expected voltage levels.

7. The method of claim 1, wherein determining the electrical signal levels at or across the plurality of electrodes generated by the at least one oscillatory signal source comprises determining a differential voltage between two segmented electrodes of the plurality of electrodes.

8. The method of claim 1, wherein determining the electrical signal levels at or across the plurality of electrodes generated by the at least one oscillatory signal source comprises:
    coupling a plurality of segmented electrodes that are at the same axial level together to form an effective ring electrode; and
    determining a differential voltage between the effective ring electrode and another ring electrode.

9. The method of claim 1, wherein repeatedly determining the error value for each of the adjusted hypothetical locations of the at least one oscillatory signal source until the determined error value is less than or equal to the threshold value comprises repeatedly determining the error value for each of the adjusted hypothetical locations of the at least one oscillatory signal source until the determined error value is minimized.

10. A medical device comprising:
a memory configured to store information indicative of electrical signal levels at or across a plurality of electrodes implanted in a brain of a patient, wherein the electrical signal levels are generated by at least one oscillatory signal source in the brain of the patient; and
processing circuitry configured to:
determine the electrical signal levels at or across the plurality of electrodes implanted in the brain of the patient based on the stored information;
determine, based on a hypothetical location of the at least one oscillatory signal source, expected electrical signal levels at the plurality of electrodes;
determine an error value based on the determined electrical signal levels and the expected electrical signal levels;
repeatedly adjust the hypothetical location, and repeatedly determine the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value;
generate information indicative of the location of the at least one oscillatory signal source; and
cause delivery of an electrical stimulation signal based on the information indicative of the location of the oscillatory signal source.

11. The medical device of claim 10, wherein the medical device comprises an implantable medical device.

12. The medical device of claim 10, wherein the medical device comprises a programmer.

13. The medical device of claim 10, wherein the location of the at least one oscillatory signal source is equal to the hypothetical location for the at least one oscillatory signal source for which the determined error value is less than or equal to the threshold value.

14. The medical device of claim 10, wherein the processing circuitry is configured to:
determine which electrodes of the plurality of electrodes are most proximal to the at least one oscillatory signal source based on the location of the at least one oscillatory signal source; and
generate information indicative of the determined electrodes.

15. The medical device of claim 10, wherein to cause delivery of the electrical stimulation signal, the processing circuitry is configured to cause the determined electrodes to deliver the electrical stimulation signal.

16. The medical device of claim 10, wherein to determine, based on the hypothetical location of the at least one oscillatory signal source, expected electrical signal levels at the plurality of electrodes, the processing circuitry is configured to determine the expected electrical signal levels based on lead-field equations that define one or more relationships between the expected electrical signal levels and the hypothetical location.

17. The medical device of claim 16, wherein the lead-field equations define a plurality of distance scalar values based on coordinates of the electrodes and coordinates of the hypothetical location, wherein the determined electrical signals comprise a plurality of measured voltage levels, and wherein to determine the error value based on the determined electrical signal levels and the expected electrical signal levels, the processing circuitry is configured to:
determine an expected charge value for the at least one oscillatory signal source based on the distance scalar values and the measured voltage levels;
multiply the expected charge value and the measured voltage levels to determine a plurality of expected voltage values; and
determine the error value based on a difference between the measured voltage levels and expected voltage levels.

18. The medical device of claim 10, wherein to determine the electrical signal levels at or across the plurality of electrodes generated by the at least one oscillatory signal source, the processing circuitry is configured to determine a differential voltage between two segmented electrodes of the plurality of electrodes.

19. The medical device of claim 10, wherein to determine the electrical signal levels at or across the plurality of electrodes generated by the at least one oscillatory signal source, the processing circuitry is configured to:
cause coupling of a plurality of segmented electrodes that are at the same axial level together to form an effective ring electrode; and
determine of a differential voltage between the effective ring electrode and another ring electrode.

20. The medical device of claim 10, wherein to repeatedly determine the error value for each of the adjusted hypothetical locations of the at least one oscillatory signal source until the determined error value is less than or equal to the threshold value, the processing circuitry is configured to repeatedly determine the error value for each of the adjusted hypothetical locations of the at least one oscillatory signal source until the determined error value is minimized.

21. A system comprising:
one or more leads comprising electrodes implanted in a brain of a patient;
a sensing circuitry configured to sense electrical signal levels at or across a plurality of the electrodes, wherein the electrical signal levels are generated by at least one oscillatory signal source in the brain of the patient; and
processing circuitry configured to:
determine the electrical signal levels based on information indicative of the sensed electrical signals from the sensing circuitry;
determine, based on a hypothetical location of the at least one oscillatory signal source, expected electrical signal levels at the plurality of electrodes;
determine an error value based on the determined electrical signal levels and the expected electrical signal levels;
repeatedly adjust the hypothetical location, and repeatedly determine the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value;
generate information indicative of the location of the at least one oscillatory signal source; and cause delivery of an electrical stimulation signal based on the information indicative of the location of the oscillatory signal source.

22. The system of claim 21, wherein the system comprises an implantable medical device, wherein the implantable medical device comprises the sensing circuitry and the processing circuitry.

23. The system of claim 21, wherein the system comprises an implantable medical device and a programmer, wherein the implantable medical device comprises the sensing circuitry and the programmer comprises the processing circuitry.

24. A computer-readable storage medium comprising instructions stored thereon that when executed by one or more processors of a medical device to cause the one or more processors to:
  determine electrical signal levels at or across a plurality of electrodes implanted in a brain of a patient, wherein the electrical signal levels are generated by at least one oscillatory signal source in the brain of the patient;
  determine, based on a hypothetical location of the at least one oscillatory signal source, expected electrical signal levels at the plurality of electrodes;
  determine an error value based on the determined electrical signal levels and the expected electrical signal levels;
  repeatedly adjust the hypothetical location, and repeatedly determine the error value for each of the adjusted hypothetical locations of the at least one oscillatory signal source until the determined error value is less than or equal to a threshold value, wherein a location of the at least one oscillatory signal source is based on a hypothetical location for the at least one oscillatory signal source for which the determined error value is less than or equal to the threshold value;
  generate information indicative of the location of the at least one oscillatory signal source; and
  cause delivery of an electrical stimulation signal based on the information indicative of the location of the oscillatory signal source.

25. The computer-readable storage medium of claim 24, further comprising instructions that cause the one or more processors to:
  determine which electrodes of the plurality of electrodes are most proximal to the at least one oscillatory signal source based on the location of the at least one oscillatory signal source; and
  generate information indicative of the determined electrodes.

* * * * *